United States Patent [19]
Ideker et al.

[11] Patent Number: 5,222,501
[45] Date of Patent: Jun. 29, 1993

[54] METHODS FOR THE DIAGNOSIS AND ABLATION TREATMENT OF VENTRICULAR TACHYCARDIA

[75] Inventors: Raymond E. Ideker, Durham, N.C.; Gregory P. Walcott, Palmyra, Pa.

[73] Assignee: Duke University, Durham, N.C.

[21] Appl. No.: 829,457

[22] Filed: Jan. 31, 1992

[51] Int. Cl.$^5$ .............................................. A61B 8/12
[52] U.S. Cl. ............................ 128/660.03; 128/786; 128/662.06
[58] Field of Search ..................... 128/660.03, 662.06, 128/784, 786

[56] References Cited

U.S. PATENT DOCUMENTS

| | | | |
|---|---|---|---|
| 4,862,887 | 9/1989 | Weber et al. | 128/786 |
| 4,928,695 | 5/1990 | Goldman et al. | 128/786 |
| 4,936,281 | 6/1990 | Stasz | 128/660.03 |
| 4,940,064 | 7/1990 | Desai | 128/786 |
| 5,010,886 | 4/1991 | Passafaro et al. | 128/662.06 |
| 5,056,517 | 10/1991 | Fenici | 128/786 |

OTHER PUBLICATIONS

Bolick, et al., *Circulation* 74, No. 6, Dec. (1986).
Downwar, et al., "Multi–Use" Reentry in a Functional Sheet of Surviving Subendocardium (2:45), *Supplement to Journal of the American College of Cardiology* 17, No. 2., (Supplement A), Feb. (1991).
T. Ferguson et al., *Surgical Therapy for Cardiac Arrhythmias, Current Topics in Cardiology*, (1991).
B. Barzilai et al., *J. Am. Soc. Echo.* 1, 179–186 (1988).
A. Harris et al., *Exp. Med. Surg.* 1, 105 (1943).
F. Witkowski et al., *Am. J. Physiol.* 254, H804 (1988).
P. Wolf et al., A Method of Measuring Cardiac Defibrillation Potentials, Proc. ACEMB Baltimore, Md, 4, (1986) (The alliance for Engineering in Medicine and Biology, Publishers).
W. Smith et al., *Proceedings of Computers in Cardiology*, 131 (1982) (IEEE Computer Society).
P. Wolf et al., *Proc. ACEMB Washington, DC*, 124 (1985).
T. Funada et al., *Med. Biol. Eng. Comput.* 21, 418 (1983).
D. Frazier et al., *Circ. Res.* 63, 147 (1988).

*Primary Examiner*—William E. Kamm
*Assistant Examiner*—George Manuel
*Attorney, Agent, or Firm*—Bell, Seltzer, Park & Gibson

[57] ABSTRACT

A closed-heart method for treating ventricular tachycardia in a myocardial infarct patient afflicted with ventricular tachycardia is disclosed. The method comprises, first, defining a thin layer of spared myocardial tissue positioned between the myocardial infarct scar tissue and the inner surface of the myocardium (the endocardium) of the patient, and then ablating the thin layer of spared myocardial tissue by a closed-heart procedure with an ablation catheter. Apparatus for carrying out the method is also disclosed.

Also disclosed is a method for prognosing the likelihood of ventricular tachycardia occuring in a myocardial infarct patient not previously diagnosed as afflicted with ventricular tachycardia. The method comprises detecting a thin layer of spared myocardial tissue positioned between the myocardial infarct scar tissue and the inner surface of the myocardium (the endocardium) in the patient.

38 Claims, 15 Drawing Sheets

SURGERY

CATHETER ABLATION

METHODS FOR THE DIAGNOSIS AND ABLATION TREATMENT OF VENTRICULAR TACHYCARDIA

This invention was made with Government support under grant numbers HL-28429, HL-17670, and HL-33637 from the National Institutes of Health and grant number CDR-8622201 from the National Science Foundation. The Government has certain rights to this invention.

FIELD OF THE INVENTION

This invention relates to methods for the ablation of cardiac tissue for the treatment of ventricular tachycardia and to diagnostic methods for detecting conditions which indicate a high risk of ventricular tachycardia.

BACKGROUND OF THE INVENTION

Ventricular tachycardia is a disease of the heart in which the heart's normal rhythmic contraction is altered, thus affecting heart function. The condition is often described as a heart beat which is too fast, although the disease is far more complex. Ventricular tachycardia occurs most often in patients following a myocardial infarction. A myocardial infarction, commonly referred to as a heart attack, is a loss of blood flow to a region of the heart causing the myocardial (muscle) tissue in that region to die and be replaced by an area of scar tissue known as a myocardial infarct. In most cases, this occurs in the left ventricle.

Ventricular tachycardia ("VT") may be initiated and sustained by a re-entrant mechanism, termed a "circus" movement. The mechanism of re-entry, as it is currently understood, is discussed in M. Josephson and H. Wellens, *Tachycardias: Mechanisms, Diagnosis, Treatment*, Chap. 14 (1984)(Lea & Febiger). Most cases of sudden cardiac death that have occurred during cardiac monitoring have begun as VT that degenerated into ventricular fibrillation.

While VT can be halted after it begins by pacing or cardioversion, it is preferable to prevent the arrhythmia from arising. Drug therapy has been used, but is successful in only 30 to 50 percent of patients and has undesirable side effects. Endocardial resection, a surgical procedure involving removing the tissue in the ventricle thought to be the source of the VT, has been reported to eradicate VT in up to 90 percent of patients, but it suffers from a 5 to 10 percent incidence of perioperative mortality. For a discussion of surgical procedures, see T. Ferguson and J. Cox, Surgical Therapy for Cardiac Arrhythmias, in *Nonpharmacological Therapy of Tachyarrhythmias* (G. Breithardt et al. eds. 1987).

As an alternative to surgery, the technique most often attempted is ablation. Typically, programmed premature pacing is performed from a catheter electrode in the right or left ventricular cavity. During programmed premature pacing, a stimulus, usually of twice diastolic threshold, is repeatedly given prematurely until either VT is induced or the tissue is too refractory to be excited. The ECG is examined during induced VT and compared to the ECG showing spontaneous bouts of VT. If the ECG is similar, it is assumed that the patient's clinical VT is being induced. A mapping catheter in the left ventricular cavity is used to record from numerous sites sequentially to determine the activation sequence along the left ventricular endocardium during the induced VT. The site from which activation appears to originate during the induced VT is identified and assumed to be a portion of the reentrant pathway. The techniques of pace mapping and entrainment may then be used in an attempt to confirm or refine the localization of the region rising to VT. The region is then ablated. Unfortunately, this technique is usually unsuccessful unless repeated many times. For example, it has been reported by Downar et al. that for a similar technique (the electrodes were located on an endocardial balloon instead of a catheter), anywhere from 10 to 42 shocks through different electrodes were required to prevent the reinduction of VT. It is assumed that failures occur because ablation is not performed at the correct site or does not create a lesion deep enough within the ventricular wall to reach the reentrant pathway.

It is extremely desireable to prognose the likelihood of a myocardial infarct patient being susceptible to ventricular tachycardia. U.S. Pat. No. 4,680,708 to M. Cain and B. Sobel suggests a method and apparatus for analyzing electrocardiogram signals to prognose ventricular tachycardia, but the early detection of myocardial infarct patients susceptible to ventricular tachycardia remains a problem.

In view of the foregoing, an object of the present invention is to provide a technique which is effective in combatting VT, does not require the administration of drugs, and does not require open-heart surgery.

A further object of the present invention is to provide a means for prognosing the likelihood of ventricular tachycardia occuring in a myocardial infarct patient not previously diagnosed as having ventricular tachycardia.

SUMMARY OF THE INVENTION

The present invention is based on the concept that a thin layer of viable myocardial tissue adjacent to the endocardium in a myocardial infarct patient is capable of supporting multiple re-entrant pathways, any one of which can give rise to ventricular tachycardia.

In view of the foregoing finding, a first aspect of the present invention is a closed-heart method for treating ventricular tachycardia in a myocardial infarct patient afflicted with ventricular tachycardia. The method comprises, first, defining a thin layer of spared myocardial tissue positioned between the myocardial infarct scar tissue and the inner surface of the myocardium (the endocardium) of the patient, and then ablating the thin layer of spared myocardial tissue by a closed-heart procedure with an ablation catheter.

In a particular embodiment of the foregoing, the ablating step is carried out by creating at least one elongate lesion in said thin layer extending from the endocardium to the myocardial infarct scar tissue in a closed-heart procedure with an ablation catheter. The at least one elongate lesion is configured to reduce the size, in surface area, of any portion of the thin layer in electrical contact with the remainder of the endocardium sufficient to combat ventricular tachycardia in said patient. This may be carried out by electrically separating from the remainder of the endocardium a portion of the thin layer which has a size, in surface area, sufficient to combat ventricular tachycardia (e.g., by creating a continuous elongate lesion around the thin layer of spared myocardial tissue, the continuous lesion encircling the thin layer to electrically separate the thin layer from adjacent myocardial tissue), or by creating at least one (or a plurality) of elongate lesions in the thin layer, wherein the at least one elongate lesion divides the the layer into a plurality of electrically separated portions, with the capability of each portion for originating ventricular tachycardia being reduced sufficiently to combat ventricular tachycardia in the patient.

Another aspect of the present invention is an apparatus for the ablation treatment of ventricular tachycardia. The apparatus comprises an intraventricular catheter, a detecting means for detecting a thin layer of spared endocardial tissue connected to the intraventricular catheter, an ablation means for ablating the thin layer of spared endocardial tissue connected to the intraventricular catheter; and an analyzing means operatively associated with the detecting means for prognosing the likelihood of ventricular tachycardia arising from the thin layer.

Another aspect of the present invention is a method for prognosing the likelihood of ventricular tachycardia occuring in a myocardial infarct patient not previously diagnosed as afflicted with ventricular tachycardia. The method comprises detecting a thin layer of spared myocardial tissue positioned between the myocardial infarct scar tissue and the inner surface of the myocardium (the endocardium) in the patient.

Previous work in the diagnosis and treatment of ventricular tachycardia has always looked for functional or electrical characteristics of tissue rather than a specific anatomic structure. The present invention, in contrast, is based on the finding that a specific macroscopic anatomical structure gives rise to ventricular tachycardia.

DETAILED DESCRIPTION OF THE INVENTION

Figure 1:
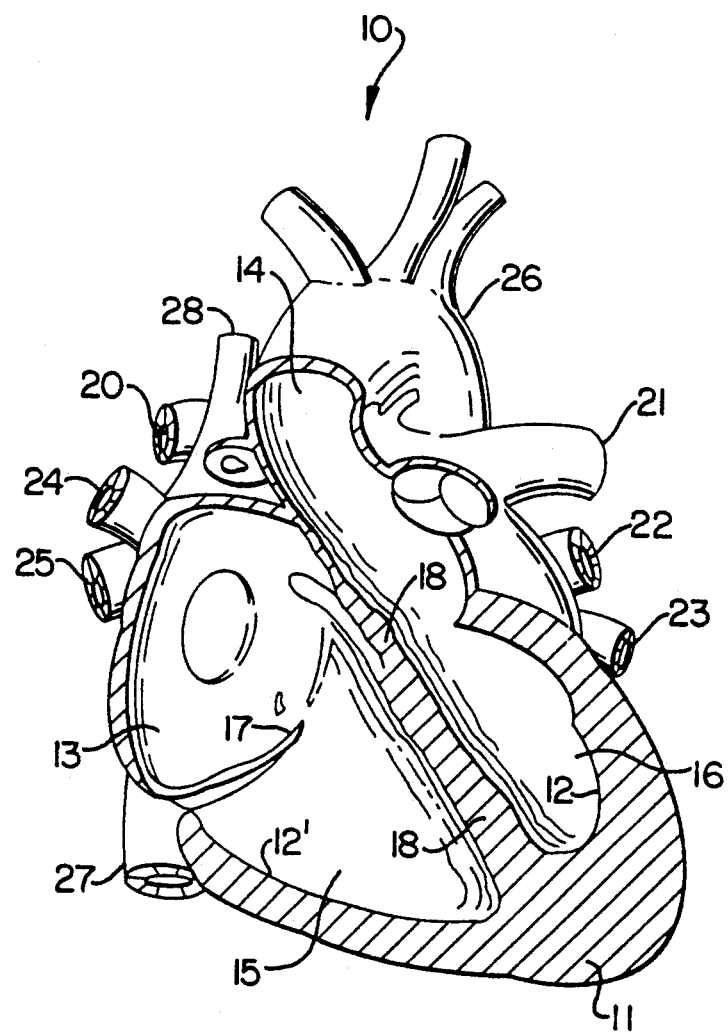
FIG. 1 is a side view of a human heart, with portions cut away to reveal the internal chambers and myocardial walls.

The basic anatomy of the human heart 10 is illustrated in FIG. 1. Its walls are composed primarily of myocardial (muscle) tissue. The muscle tissue walls of the heart are referred to as the myocardium 11. The inner surface of the myocardium, which is in contact with the blood in the heart chambers, is the endocardium 12,12'. The heart is longitudinally divided into left and right halves. Each half has an upper chamber called an atrium 13,14, and a lower chamber called a ventricle 15,16. Between the atrium and the ventricle of each half is an atrioventricular (AV) valve 17 which is a one way valve allowing blood flow only from the atrium into the ventricle. The right and left ventricles are separated by the interventricular septum 18.

The circulatory system is comprised of two separate systems, pulmonary and systematic circulation. In the pulmonary circuit blood is pumped by the right ventricle 15 into the pulmonary artery which then splits into a right pulmonary artery 20 and a left pulmonary artery 21 allowing to flow through the lungs and then into the pulmonary veins 22,23,24,25 which flow into the left atrium 14. The oxygen rich blood from the pulmonary circuit is pumped by the left ventricle into the systemic circuit via the aorta. After passing throughout the body, the blood returns to the right atrium via the inferior vena cava and the superior vena cava.

The thickness of the walls of the chambers of the hearts vary in relation to the amount of pumping work they perform. The atria 13, 14 are of little importance in pumping the blood except under high demand conditions, such as exercise, and are thin walled (2-3 millimeters). The right ventricle 15 only pumps blood through the relatively short pulmonary circuit and is significantly more thin walled than the left ventricle 16 which must maintain the pressure within the systemic circuit (8-12 millimeters).

Figure 2A:
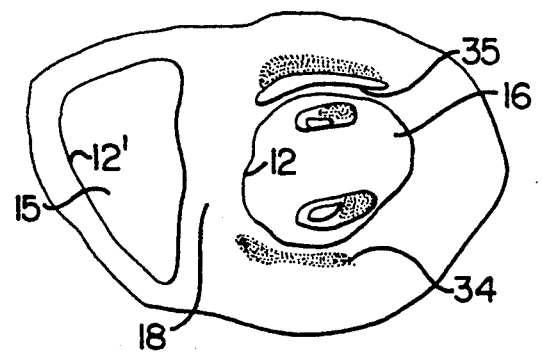
FIGS. 2A, 2B, 2C illustrate typical cross-sectional slices from control (FIG. 2A), subacute ventricular tachycardia (FIG. 2B), and chronic ventricular tachycardia (FIG. 2C) groups.
Figure 2B:
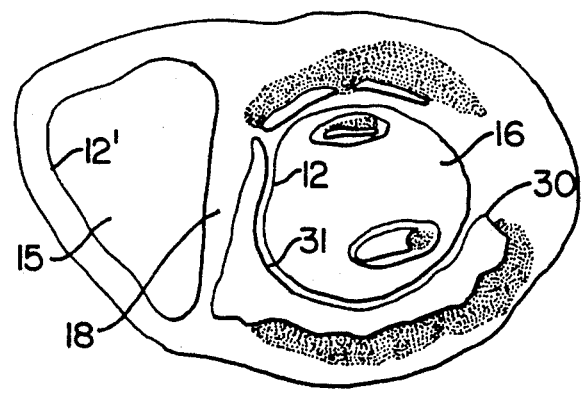
Figure 2C:
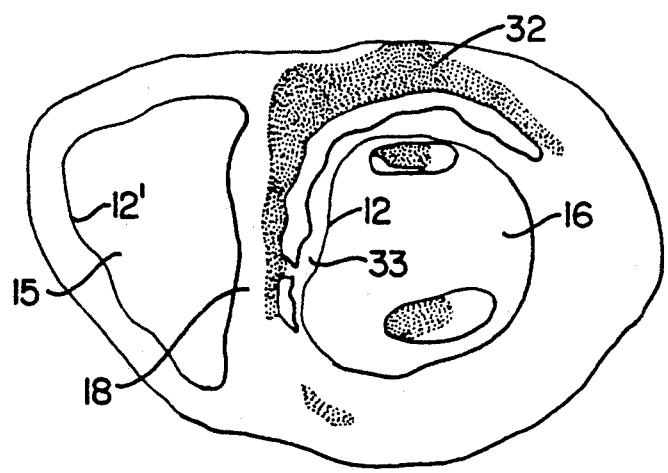

FIG. 2 illustrates typical cross-sectional slices of ventricles from patients with myocardial infarction but no ventricular tachycardia (control) (FIG. 2A), patients with subacute myocardial infarction with ventricular tachycardia (FIG. 2B), and patients with chronic myocardial infarction with ventricular tachycardia (FIG. 2C) groups. The subacute group had predominantly large solid myocardial infarcts 30 with ribbon spared subendocardium 31. The chronic ventricular tachycardia group has predominantly large patchy myocardial infarcts 32 with irregular spared subendocardium. The control group had smaller hearts and smaller more randomly distributed patchy myocardial infarcts 34 with little ribbon spared subendocardium 35. Black represents solid myocardial infarct, and stippling represents patchy myocardial infarct. Slices are seen from the basal aspect. These data are known. See D. Bolick et al., *Circulation* 74, 1266, 1273 (1986).

The thin layer referred to herein is a layer of surviving myocardial tissue located between the surface of the endocardium 12,12' and the myocardial infarct scar tissue. The thin layer may be in the right or left ventricle, but more typically the left ventricle. A layer of fibrosis may be positioned beneath the thin layer, as explained below. While the precise dimensions of the thin layer will vary from patient to patient, with some variability due to the variability of the infarct in the epicardial to endocardial dimension, the thin layer will generally have a thickness of up to about 5 millimeters, and will generally have an endocardial surface area of at least 15 square centimeters. Typically, the thin layer will have a thickness of from about 0.25 to 2 millimeters, and will have an endocardial surface area of from about 20 to 40 square centimeters.

The present invention is directed to both diagnostic and treatment methods for ventricular tachycardia in a patient afflicted with a myocardial infarct. The treatment method of the present invention involves first, defining a thin layer of spared myocardial tissue positioned between the myocardial infarct scar tissue and the inner surface of the myocardium (the endocardium) of the patient, and then ablating the thin layer of spared myocardial tissue. The diagnostic method provides a means for examining myocardial infarct patients to determine their risk of developing ventricular tachycardia by detecting the presence of a thin layer of spared myocardial tissue positioned between the myocardial infarct scar tissue and the inner surface of the myocardium (the endocardium).

Reentrant pathways causing VT may arise from numerous sites within the thin layer of spared tissue between the infarct and the endocardium, the first or defining step involves identifying the presence and location of this thin layer instead of inducing and mapping the activation sequence during a particular incidence of induced VT as was done previously. Thus, the subject on which the defining step is performed need not have VT induced prior to the procedure, and need not be in VT during the defining step.

The thin layer can be defined by any one or a combination of several techniques, including (1) analyzing recordings during regular rhythm from electrodes on a catheter; (2) pacing from an electrode on the catheter and analyzing the pacing threshold as well as recordings of the pacing stimulus and the ensuing activation sequence from other electrodes on the same catheter; (3) direct visualization of the thin layer of spared myocardial tissue by an imaging technique such as echocardiography/ultrasound which can differentiate healthy myocardial tissue from infarcted tissue; (4) detecting by echocardiography the infarct itself overlying the thin layer of spared myocardial tissue (e.g., by detecting altered heart wall motion overlying the infarct or by detecting altered backscatter from the infarct); (5) visualization of endocardial fibrosis beneath the thin layer of spared myocardial tissue (i.e., between the thin layer of spared myocardial tissue and the ventricular cavity); and (6) electrically stimulating the endocardium to detect an increased pacing threshold (due to the presence of endocardial fibrosis overlying the thin layer of spared myocardial tissue).

Any suitable apparatus may be employed to carry out the defining step, such as a catheter mounted echocardiographic ultrasound crystal sensor inserted into the interior of the heart of said patient, an echocardiographic ultrasound crystal sensor positioned in the esophagus of the patient, or echocardiographyic ultrasound crystal sensor applied to the chest wall by contact to the skin. The imaging device need not be on a catheter (is in the case of an esophageal echocardiograph), though preferably the mapping is performed with a catheter mounted sensing device. Particularly suitable is an echocardiagraphic/ultrasound crystal sensor mounted on a catheter which is inserted into the interior of the heart of the patient. This same catheter can also carry the ablation device as discussed below. Suitable detection devices are known, examples of which are disclosed in U.S. Pat. No. 5,000,185 and in PCT Application Number WO 91/02488. (Applicants intend that all U.S. Patent references cited herein be incorporated herein by reference). An ultrasonic technique for mapping myocardial tissue with an external sensor is discussed in B. Barzilai et al., *J. Am. Soc. Echo.* 1, 179-186 *(1988)*(showing altered backscatter from myocardial infarct).

Figure 3A:
FIGS. 3A-3F schematically illustrates various ablation patterns on the internal surface of the heart which may be employed in carrying out the present invention.
Figure 3B:
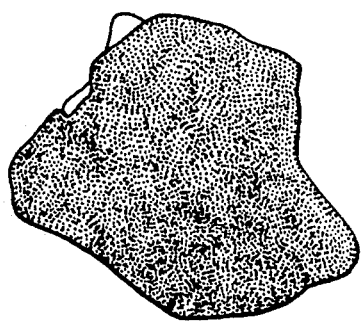
Figure 3C:
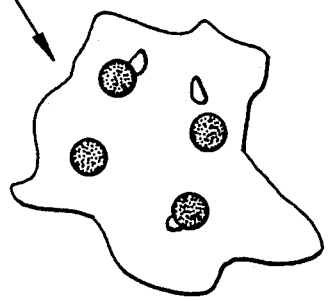
Figure 3D:
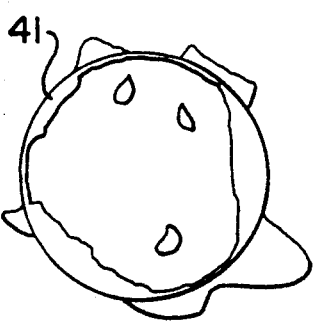
Figure 3E:
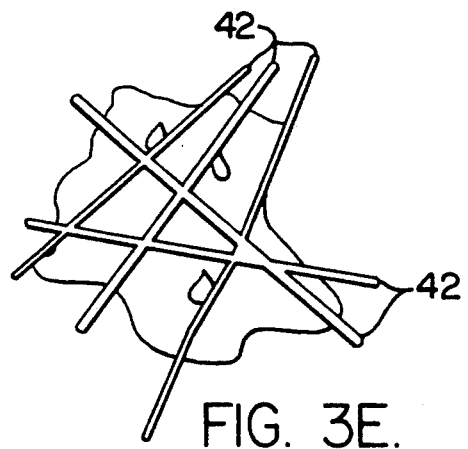
Figure 3F:
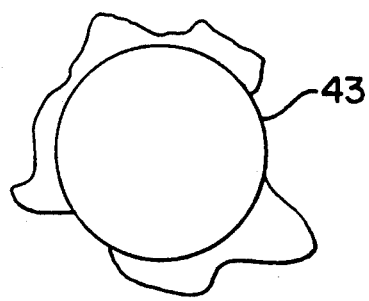

Once the thin layer of spared myocardium is identified, it can be ablated by a variety of methods. Three such methods of the present invention, along with prior art methods, are schematically illustrated in FIG. 3. The endocardial surface is schematically illustrated in FIG. 3A, the prior art surgical resection technique is illustrated in FIG. 3B, and prior art catheter ablation techniques are schematically illustrated in FIG. 3C. In the embodiment of the invention illustrated in FIG. 3D, ablation is accomplished by creating a continuous lesion 41 extending from the endocardium to the myocardial infarct scar tissue around the thin layer of spared myocardial tissue. This continuous lesion encircling the thin layer electrically isolates the thin layer from adjacent myocardial tissue so that any arrhythmias arising in the thin layer are not able to propagate into the rest of the heart. In the embodiment of the invention illustrated in FIG. 3E, ablation is accomplished by creating at least one, or as illustrated a plurality of, elongate lesions 42 in the thin layer, with each lesion extending from the endocardium to the myocardial infarct scar tissue. The elongate lesion(s) are patterned to divide the thin layer into a plurality of electrically separated portions each, of which is substantially incapable of originating ventricular tachycardia. In the embodiment of the invention illustrated in FIG. 3F, ablation is accomplished by destroying all of the thin layer of spared myocardial tissue with a large lesion 43.

A variety of devices are known and available for performing the ablation step. A direct current ablation electrode such as that disclosed in U.S. Pat. No. 4,896,671 or a laser ablation catheter such as that disclosed in U.S. Pat. No. 4,985,028 may be used. More preferably, a radio frequency (RF) ablation catheter as disclosed in U.S. Pat. No. 4,945,912 or a microwave ablation catheter such as that discussed in J. Langberg et al., *Pace* 14, 2105 (December, 1991) is used. Another approach is to ablate the thin layer with ultrasound at high energy, as discussed in greater detail below.

Figure 4:
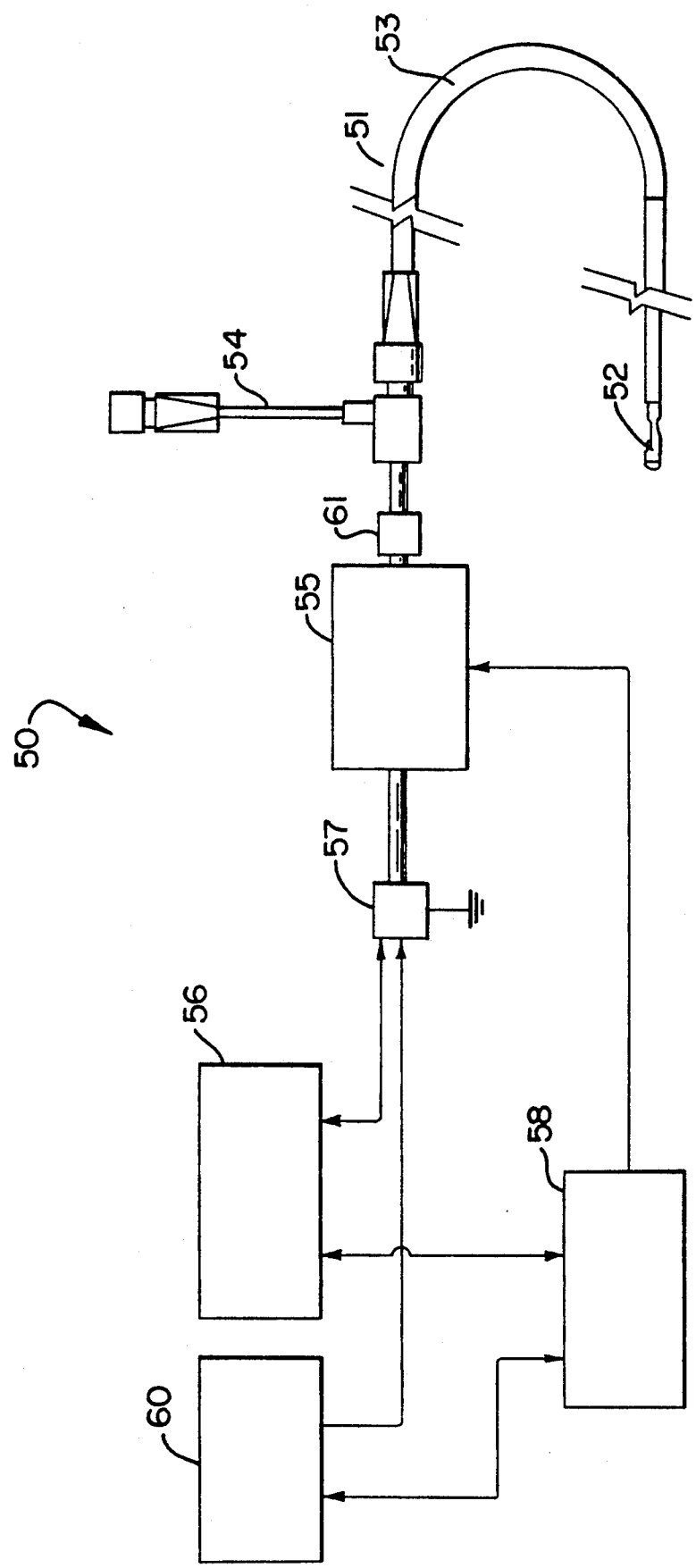
FIG. 4 schematically illustrates an apparatus useful for carrying out the ablation method of the present invention.

As noted above, both the detecting means such as an echocardiagraphic/ultrasound crystal sensor and an ablation means such as a laser unit may advantageously be located on the same catheter. Examples of such catheter devices are disclosed in U.S. Pat. No. 5,000,185, U.S. Pat. No. 4,936,281 and in PCT Application Number WO 91/02488. A schematic diagram of such a catheter device using and ultrasound sensing means and a laser ablation means is shown in FIG. 4. The system 50 includes a catheter probe assembly 51 including a distal subassembly 52 inserted within a guide catheter 53. The proximal end of the guide catheter 53 is coupled to a conventional side arm connector 54. The distal subassembly 52 is coupled to a suitable motor means 55 which provides the drive to maneuver the distal subassembly 52. The ultrasonic imaging components within the distal subassembly 52 are electrically connected with an electroacoustic transducer and an ultrasound transceiver 56 via suitable electrical contact brushes 57. To perform detection the ultrasonic imaging components within the distal subassembly are activated and the received signals are processed by the ultrasound transceiver 56. The signals are further processed by algorithms performed by the computer 58 to generate an image of the tissue structures reflecting the ultrasonic energy toward the distal subassembly 52. The ablating is performed by a laser means. A laser driver 60 provides a source of laser radiation which passes via the contact brushes 57 to a dual function electrical/optical connector 61 which couples the ultrasonic imaging components and laser optical components within the distal subassembly 52 to the ultrasound transceiver 56 and the laser driver 60. The computer 58 also functions to allow the operator to control the laser driver to perform ablation of tissue where desired.

A software program running in the computer 58, which computer is operatively associated with the detecting means, provides a means for prognosing the likelihood of ventricular tachycardia arising from said thin layer. In a typical embodiment of this method, the detecting step includes determining if a thin layer of spared tissue exists between the infarct scar tissue and the endocardium, then creating an anatomical map of the locations of the thin layer identified to define the thin layer areas, and then evaluating the dimensions of the thin layer areas to determine if the contiguous portions of these areas are of sufficient size to support reentrant pathways.

Another option in an apparatus of the present invention is, as noted above, to use ultrasound energy at higher power levels to ablate the thin layer of tissue. An intraventricular catheter for accomplishing this method would have two sets of ultrasound crystal connected thereto: one set configured for detecting the thin layer, and another set configured for ablation of the thin layer.

Figure 5:
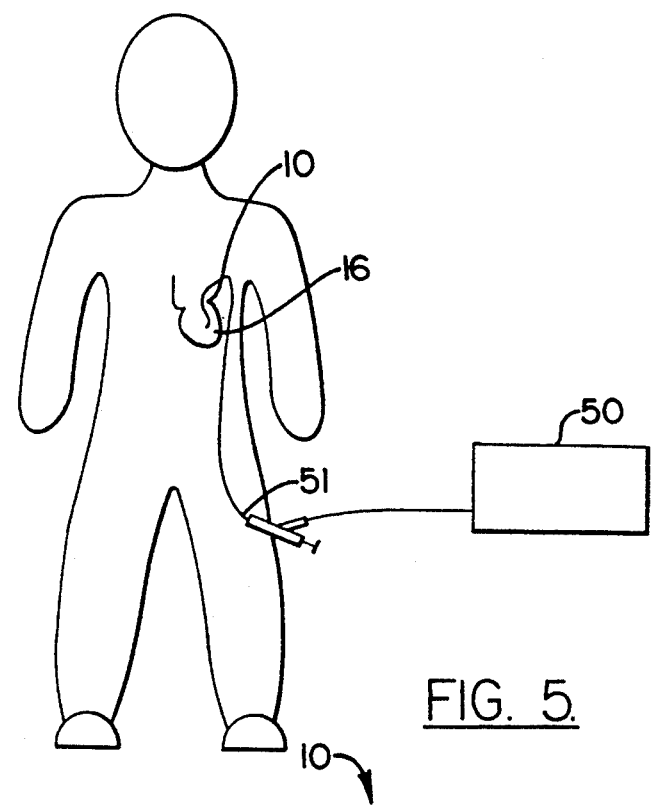
FIGS. 5-6 illustrate the use of an apparatus as given in FIG. 4.
Figure 6:
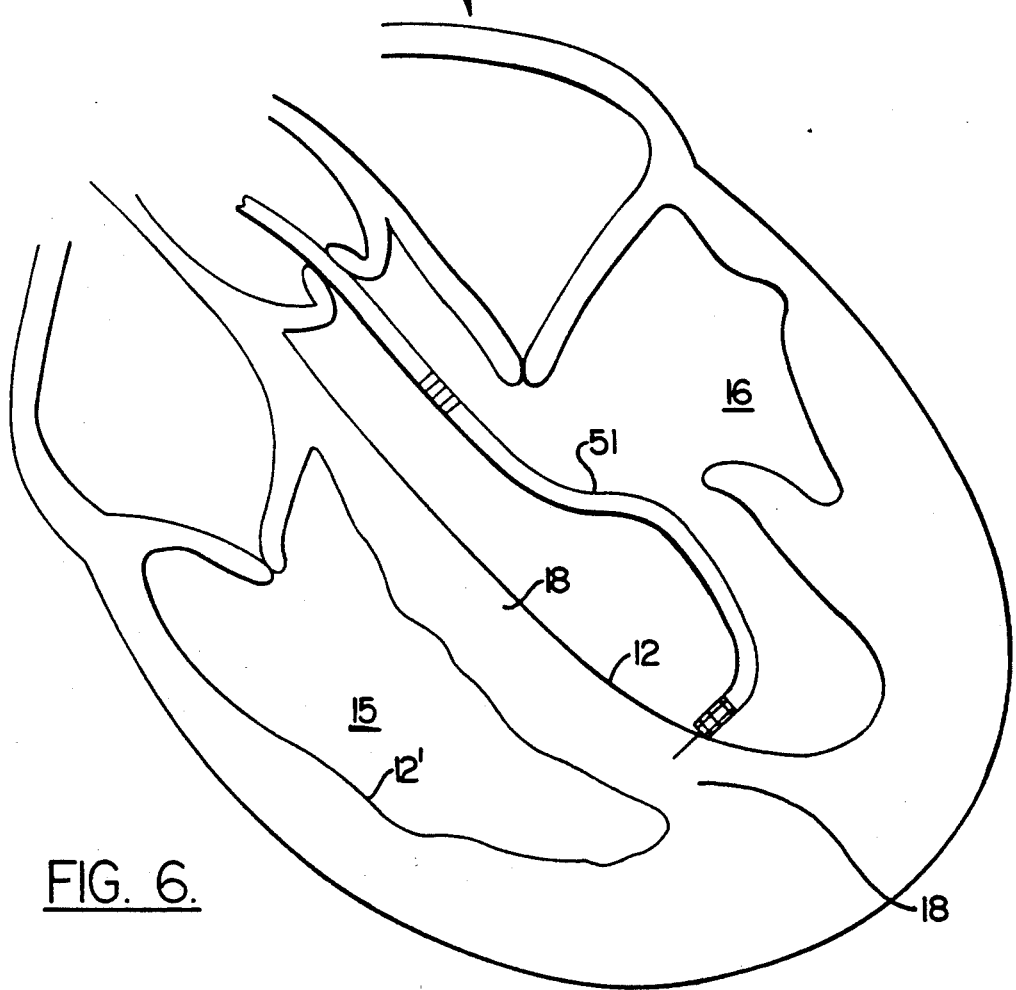

FIGS. 5–6 illustrate the use of a catheter of FIG. 4 in a method of the present invention. The catheter 51 is first introduced into the circulatory system, preferably through a vessel in the leg, and advanced into the heart 10. In the typical case of a patient suffering from VT following a myocardial infarction, the infarct scar tissue is located in the left ventricle 16, either within the outer walls of the ventricle or within the interventricular septum 18. In such a patient, the catheter is advanced into the left ventricle 16, for example by advancing the catheter into the femoral artery and then through the aorta 26 into the left ventricle 16. The detecting means is then activated and the catheter is manipulated substantially throughout the left ventricle 16 to locate any areas of thin layers of surviving tissue between the endocardium 12 and the infarct scar tissue. Preferably, this information is generated for substantially the entire area affected and then the catheter is withdrawn.

In the treatment of the present invention, each thin layer area located is rendered substantially incapable of supporting VT by the ablating step. The ablating step may be performed for all the thin layer areas found after the mapping is completed or, more preferably, is performed on each contiguous thin layer area once the area is defined. The portions of tissue to be ablated depends upon the embodiment of the present invention utilized as was discussed previously.

The ablating step is optionally followed by the step of verifying that the thin layer of spared myocardial tissue is no longer capable of originating a ventricular tachycardia. This verifying step can be accomplished using a programmed pacing technique to induce ventricular tachycardia. Such techniques are discussed in M. Josephson and H. Wellens, *Tachycardias: Mechanisms, Diagnosis, Treatment,* Chap. 14, (1984).

As noted above, the present invention further provides a method for prognosing the likelihood of ventricular tachycardia occuring in a myocardial infarct patient not previously diagnosed as afflicted with ventricular tachycardia. The method comprises detecting a thin layer of spared myocardial tissue positioned between the myocardial infarct scar tissue and the inner surface of the myocardium (the endocardium) in the patient. The thin layer to be detected is described in detail above. The procedure is advantageously carried out by closed-heart procedures, as discussed in detail above. In a typical embodiment of this method, the detecting step includes determining if a thin layer of spared tissue exists between the infarct scar tissue and the endocardium, then creating an anatomical map of the locations of the thin layer identified to define the thin layer areas, and then evaluating the dimensions of the thin layer areas to determine if the contiguous portions of these areas are of sufficient size to support reentrant pathways.

The present invention is explained further in the following Example. This Example is illustrative of the present invention, and is not to be construed as limiting thereof.

EXAMPLE 1

High Current Stimuli to the Spared Epicardium of a Large Infarct Induce Ventricular Tachycardia This study was carried out to test the hypothesis that a high current premature stimulus during the vulnerable period over the surviving epicardium of a four day old infarct in a canine model will induce sustained VT rather than ventricular fibrillation. As explained in detail below, it was found that a large S2 over a nontransmural infarct induced VT if the spared myocardium was thin.

MATERIALS AND METHODS

Surgical preparation. In twelve mongrel dogs, anesthesia was induced using intravenous thiopental sodium, 20 mg/kg, and maintained using a continuous infusion of thiopental sodium at a maintenance rate of approximately 0.8 mg/kg/min. Succinylcholine, 1 mg/kg, was also given at the time of anesthesia induction. The animals were intubated with a cuffed endotracheal tube and ventilated with room air and oxygen through a Harvard respirator (Harvard Apparatus Co. South Natick, MA). A femoral arterial line and two intravenous lines were inserted using sterile techniques. Systemic arterial pressure was continuously displayed. Arterial blood samples were drawn every 30-60 min for determination of pH, PO2, PCO2, base excess, bicarbonate, $Na^+$, $K^+$, and $Ca^{++}$ content. Ringer's lactate was continuously infused via a peripheral intravenous line. This was supplemented with sodium bicarbonate, potassium chloride, and calcium chloride as indicated to maintain pH and electrolytes within normal values. Electrocardiographic leads were applied for continuous ECG monitoring. Body temperature was maintained with a thermal mattress. With sterile surgical techniques the heart was exposed through a left thoracotomy at the fourth intercostal space; the pericardium was opened, and the left anterior descending coronary (LAD) artery was dissected free at the tip of the left atrial appendage. A noose occluder was placed around the left anterior descending artery and it was occluded by the Harris two state procedure (A. Harris and A Rojas, *Exp. Med. Surg.* 1, 105 (1943)). In order to ensure sparing of the epicardium in the entire infarct zone, partial occlusion was maintained for 30 min, followed by complete occlusion for 90 min prior to reperfusion. Five minutes before initiation of partial occlusion and again before the termination of complete occlusion the animals were pretreated with bolus injections of intravenous lidocaine (2 mg/kg). A second of lidocaine (1 mg/kg) was administered ten minutes later. The chest was closed in layers, evacuated under negative pressure and the animal was allowed to recover.

Four days after LAD occlusion, anesthesia was induced with intravenous pentobarbital (30-35 mg/kg body weight) and maintained with a continuous infusion of pentobarbital at a rate of approximately 0.05 mg/kg per min. Succinylcholine (1 mg/kg) was also given intravenously at the time of anesthesia induction. Supplemental doses of 0.25 of 0.5 mg/kg of succinylcholine were given hourly as needed to maintain muscle relaxation. The animals were ventilated, hemodynamically monitored and maintained as described above. A median sternotomy was performed, and the heart was suspended in a pericardial cradle. The recording apparatus consisted of 121 bipolar Ag-AgCl epicardial electrodes (see F. Witkowski and P. Penkoske, *Am. J. Physiol.* 254, H804 (1988)) arranged in 11 columns and 11 rows mounted in a 4×4 cm plaque. Each epicardial electrode was 1 mm in diameter. There was a 2 mm intraelectrode distance between each member of the bipolar pair and an inter-electrode distance of 4 mm. This plaque also contained a centrally located stimulating electrode. The plaque of epicardial recording electrodes was sutured over the infarcted anterior surface of the left ventricle. Four solid stainless steel wires (American Wire Gauge #30, Cooner Wire Co. Chatsworth, CA) that were insulated except at the tip were positioned for S1 pacing from the lateral right ventricle, the right ventricular outflow tract, the lateral left ventricle and the posterior left ventricle. Defibrillating patches were sutured over the right atrium and upper portion of the lateral right ventricle and the posterior apical left ventricle to deliver cardioversion or defibrillation shocks. Limb leads I, II and III were recorded with limb lead II filtered from 50 Hz to 300 Hz so it recovered quickly after large premature stimuli.

Data acquisition. A computer assisted-mapping system capable of simultaneously recording 128 channels was used to record the stimulus potentials in unipolar mode with the left leg as reference and the activation complexes in bipolar mode. See P. Wolf et al., A Method of Measuring Cardiac Defibrillation Potentials, *Proc. ACEMB Baltimore, Md.*, 4 (1986)(The Alliance for Engineering in Medicine and Biology, Publishers). Signals were recorded digitally at a rate of 1,000 samples per second with a low pass filter at 500 Hz and the high-pass filter at 5 Hz. See W. Smith et al., *Proceedings of Computers in Cardiology*, 131 (1982) (IEEE Computer Society). Gain settings for each channel were individually adjusted for optimum recording. The data were stored on videotape for off-line analysis. See P. Wolf et al., *Proc. ACEMB Washington, DC*, 124 (1985). The recordings from each channel were subsequently displayed on a SUN 3/60 work station to allow measurement of stimulus potentials and detection of activation times.

Definitions. The ventricular refractory period for a particular strength S2 was defined as the largest S1-S2 interval that failed to evoke a ventricular response. In this study inducible sustained monomorphic ventricular tachycardia was defined as an ECG sequence of uniform ventricular depolarizations at a cycle length of less than 400 ms, that lasted more than 30 sec or produced hemodynamic compromise requiring immediate cardioversion.

Stimulation protocol. Unipolar cathodal pacing at a pulse width of 5 ms was used to determine late diastolic threshold at each of the five stimulation sites (two right ventricular sites, two left ventricular sites and the center of the recording plaque). The propensity for sustained ventricular tachycardia was assessed by pacing at a cycle length of 300 ms for 10 beats (S1) at twice diastolic threshold followed by an extra stimulus (S2) consisting of a 5 ms square wave which was given to scan diastole at 5 ms intervals or less. The S1 train was delivered from one of the four pacing sites outside of the plaque of recording electrodes, while S2 was always delivered from the center of the plaque. Diastole was scanned by decreasing the S1S2 coupling interval in steps of 5 ms. The initial strength of the S2 was 10 mA. If diastole was scanned without the induction of ventricular tachycardia or ventricular fibrillation and the ventricular refractory period was reached, the strength of the S2 was increased by 10 mA and scanning was repeated. Once ventricular tachycardia or fibrillation was initiated and halted by cardioversion or defibrillation, the procedure was repeated using a new S1 site with the initial S2 strength set equal to that which induced the arrhythmia at the previous S1 site. This protocol was repeated at all four S1 sites. After ventricular dysrhythmias were initiated from all four S1 sites, the strength of the S2 was increased in 10 mA steps to a maximum of 100 mA for one of the S1 pacing sites.

Histological examination. At the end of each experiment, the heart was excised, weighed and fixed in formalin. A histological section was taken perpendicular to the epicardium through the center of the infarct zone beneath the recording plaque to determine the thickness of the infarcted and of the subepicardially spared myocardium. On either side of this perpendicular section, serial sections were taken every 0.5 mm parallel to the epicardium in the infarct zone to determine fiber orientating of the spared epicardial tissue. All sections were stained with hematoxylin and eosin.

Data analysis. The recordings from each channel were displayed on a Sun 3/60 computer work station. In all dogs the last two activations of the S1 train and all activations after the S2 stimulus until the ventricular tachycardia settled into uniform repeatable complexes on the surface ECG were analyzed. If ventricular fibrillation instead of ventricular tachycardia was induced, the initial six activation complexes after the S2 stimulus were chosen for analysis. The time selected for each activation was the fastest slope for biphasic complexes and the absolute peak value for monophasic and multiphasic complexes. T. Funada et al , Med. Biol. Eng. Comput. 21, 418 (1983). Electrodes With saturated signals or with signals too noisy to identify activations reliably were not analyzed. Isochronal maps were drawn for all complexes analyzed. A heavy black bar was used to indicate block between neighboring electrodes if 1) activation times differed by more than 40 ms (conduction velocity<0.1 m/sec), (15-17) and 2) double activations were seen in the electrodes bordering the line of block, in which one complex corresponded in time to the activation front on one side of the block and the other complex corresponded to the activation front o the other side of the line of block. Hatched bars were used to represent the "frame lines" between sequential isochronal maps. The term "frame line" is used to indicate that the activation front does not stop at the line but rather the frame lines represent the break points between maps that are necessary to represent the dynamic continuous activation sequence of reentry by a series of static discrete isochronal maps.

With voltage dividers (see P. Wolf et al., supra), potentials were measured at the 121 recording electrodes for 10 ms monophasic shocks equal in strength to the lowest current inducing the tachyarrhythmia at all four S1 sites. Potentials were also recorded for stronger shocks in increments of 20 mA to a maximum of 100 mA. unipolar potentials were measured at each recording site, relative to the preceding baseline, at a consistent point 3-4 ms into the shock. A 10 ms stimulus was used to measure the S2 potentials instead of the 5 ms stimulus used for S2 induction of the arrhythmia because a short spike, lasting 1-2 ms, was present in the recordings at the onset and the offset of the S2 stimulus. The potential gradient was calculated from the potentials and the inter-electrode distances using a finite element method. D. Frazier et al., Circ. Res. 63, 147 (1988).

Statistical procedures. Student's t test was used to analyze differences in means. Chi-square was used to analyze differences in populations. Data are presented as mean±SD. Significance was defined as $p \leq 0.05$.

RESULTS

Twelve mongrel dogs weighing 23.5±1.6 kg were the subjects of this study. One of the twelve died in the first twelve hours post LAD occlusion. A second dog died four days postinfarction during anesthesia induction for the placement of electrodes. Therefore, arrhythmia induction was attempted in ten animals. In two of the ten dogs, the S2 threshold for ventricular arrhythmia (sustained ventricular tachycardia or ventricular fibrillation) induction had only been determined for one of the S1 pacing sites before the animals died. In the remaining eight animals, the S2 arrhythmia threshold stimulus was determined for all four S1 pacing sites. Thus, the S2 arrhythmia threshold stimulus was determined for a total of 34 sites in the ten animals (Table 1). Sustained monomorphic ventricular tachycardia was induced from 24 of these sites, ventricular fibrillation from nine sites and sustained polymorphic ventricular tachycardia was induced from one S1 site. The episode of polymorphic ventricular tachycardia was eliminated from all statistical analysis. By chi-square analysis the incidence of monomorphic ventricular tachycardia was significantly different from ventricular fibrillation (p =0.03).

TABLE 1

| Dog Number | Number of S1 Sites Inducing Ventricular Tachyarrhythmias | | Transmural Extent of Infarct |
|---|---|---|---|
| | Number of Sites | | |
| | with SMVT | with VF | |
| 1 | 4 | 0 | 70% |
| 2 | 4 | 0 | 70% |
| 3 | 4 | 0 | 80% |
| 4 | 4 | 0 | 80% |
| 5* | 1 | 0 | 90% |
| 6 | 3 | 1 | 80% |
| 7 | 2+ | 1 | 80% |
| 8 | 2 | 2 | 30% |
| 9 | 0 | 4 | 20% |
| 10* | 0 | 1 | 10% |

*Died after first arrhythmic event
+Polymorphic VT from an additional S1 site
SMVT = Sustained Monomorphic Ventricular Tachycardia
VF = Ventricular Fibrillation FIG. 7 shows an example of monomorphic ventricular tachycardia induced in a dog with an 80% transmural infarct. The S1 pacing site was the right ventricular free wall and the S2 stimulus was 20 mA, which is the lowest strength S2 stimulus that induced tachycardia in this animal. The activation front initiated by S1 stimulation enters from the upper left corner which is the area closest to the S1 pacing site (FIG. 7A). The front then conducts diagonally across the tissue under the plaque, following the long axis of the myocardial fibers. The earliest activations after S2 stimulation are recorded on the left side of the plaque toward the S1 site (FIG. 7B), which is more recovered than the right and bottom sides at the time of S2 stimulation. The activation fronts then conduct to the right around both sides of a line of block (represented by the heavy black bar). There is a 71 ms time difference between the latest activation time recorded in the initial ventricular tachycardia beat (FIG. 7B) and the earliest activation time recorded in the next beat (FIG. 7C) and double complexes are recorded at these sites. Therefore, block is assumed present between the late site in FIG. 7B and the adjacent early sites in FIG. 7C, so that it is not clear how or if the first beat conducted to the second. The fact that earliest activation sites for the second ventricular tachycardia beat are not at the edge of the plaque as for the first beat, but are next to the line of assumed block, raises the possibility that reentry did occur, although it was undetected in the recordings. Activation then sweeps around the upper line of block and possibly sweeps also around the lower line of block although this is not definite because the lower line of block extends to the edge of the plaque (FIG. 7C). The latest activation tine in this beat is 31 ms before the earliest activation time recorded in the third tachycardia beat (FIG. 7D) and double complexes are no longer observed in this region. Thus reentry is assumed to occur between these two beats. The central line in FIG. 7C is shown solid to the left and hatched to the right to represent block between beats 1 (FIG. 7B) and 2 (FIG. 7C) and reentry between beats 2 (FIG. 7C) and 3 (FIG. 7D). The hatched line is a frame line between successive panels that is necessary to represent reentry by a series of isochronal maps. A similar activation pattern is seen for the next three beats (FIG. 7D-F) with slight changes in the lines of block from beat to beat. By the fifth beat, the lower line of block has shortened, so that a clear figure of 8 reentry pattern is present (FIG. 7F). The tachycardia was stable after the fifth beat with only minimal changes in the frame and block lines in subsequent activation sequences. Conduction through the isthmus stabilized after the seventh beat.

Figure 7A:
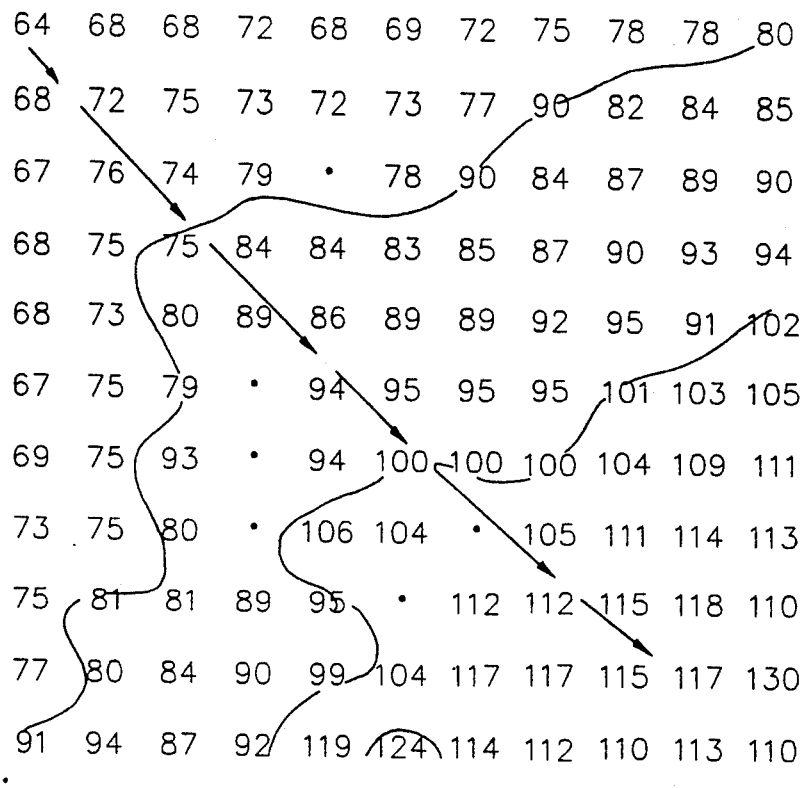
FIGS. 7A-G shows the initiation of sustained ventricular tachycardia settling into a monomorphic figure of 8 reentry pattern. The activation times and isochronal maps of the last beat of the S1 train (Panel A) are shown as well as the first 5 beats of VT (Panels B-F) induced after a 20 mA S2 stimulus at an S1S2 interval of 210 ms as recorded by a plaque of 121 bipolar electrodes over the infarct in the left ventricle. The S1S1 interval of the pacing train is 300 ms. The long axis of the spared myocardial fibers is represented by the double headed arrow at the top of the figure. Each number gives the activation time in ms at an electrode site. The isochronal interval is 20 ms. In panel A time zero is the beginning of the S1 stimulus. In Panels B-F time zero is the beginning of the S2 stimulus. In panel B, the first beat after S2 stimulation, arrows indicate that the activation fronts conduct around both sides of a line of block (reepresented by the heavy black bar in this and subsequent figures). The hatched line (in this and subsequent figures) represents a frame line between panels in which reentry is believed to occur. In panel C, the adjoining solid and hatched lines indicate block between beats one and two and reentry between beats two and three respectively. Panel 2 shows the monomorphic ventricular tachycardia as recorded by the surface leads I, II and III. Closed arrow indicates S2.
Figure 7B:
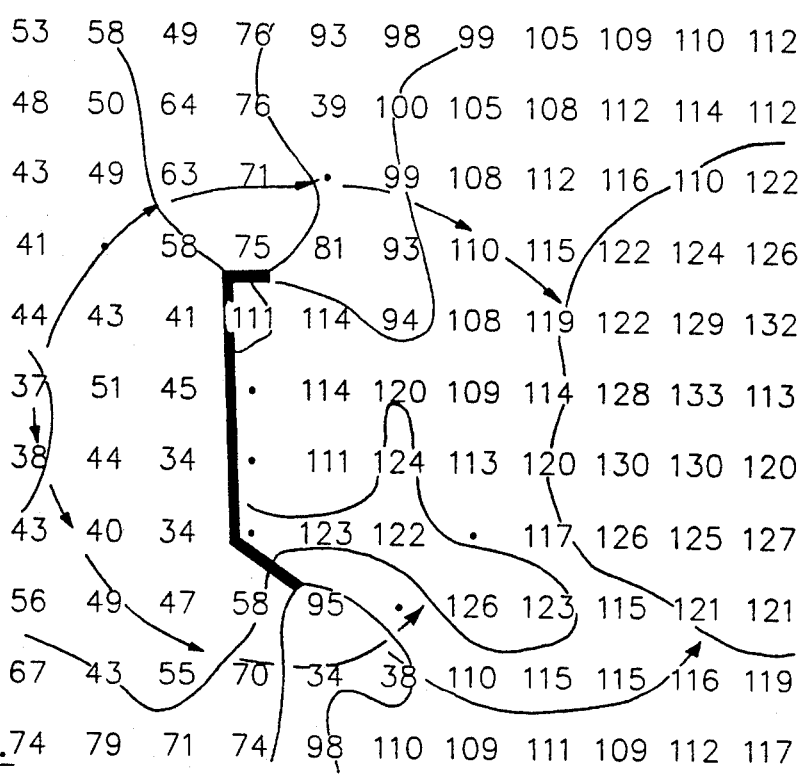
Figure 7C:
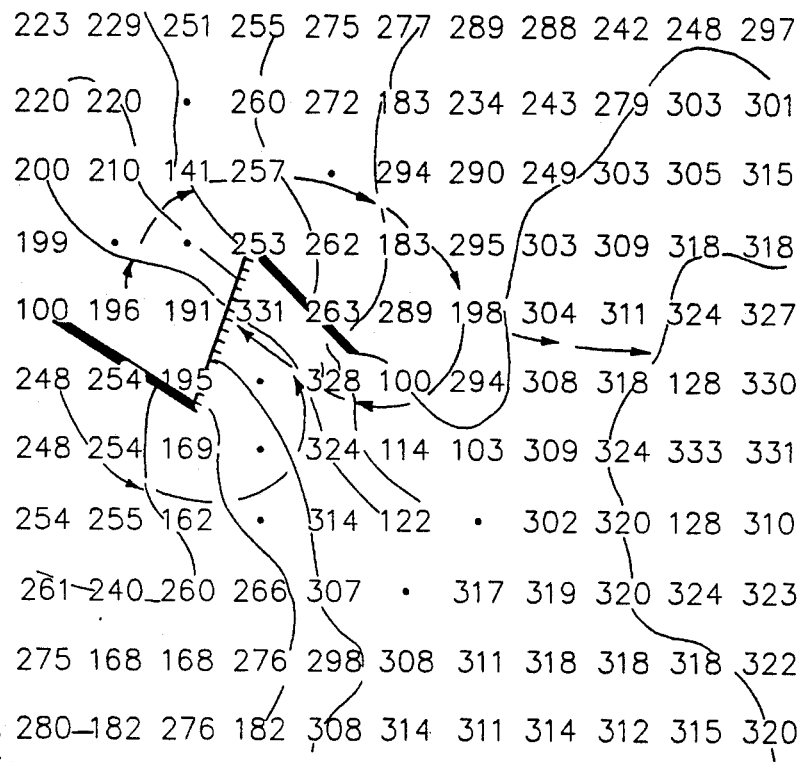
Figure 7D:
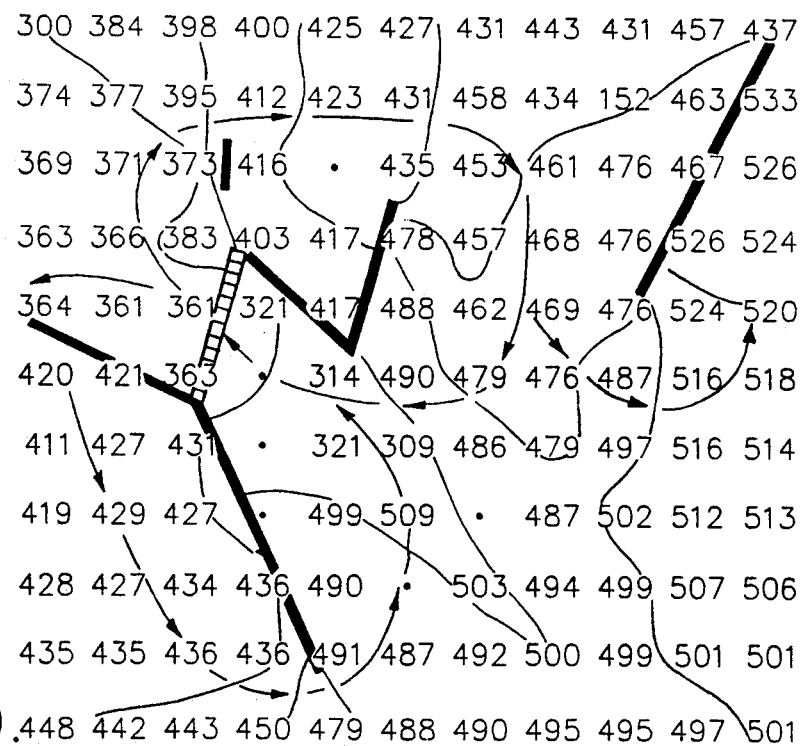
Figure 7E:
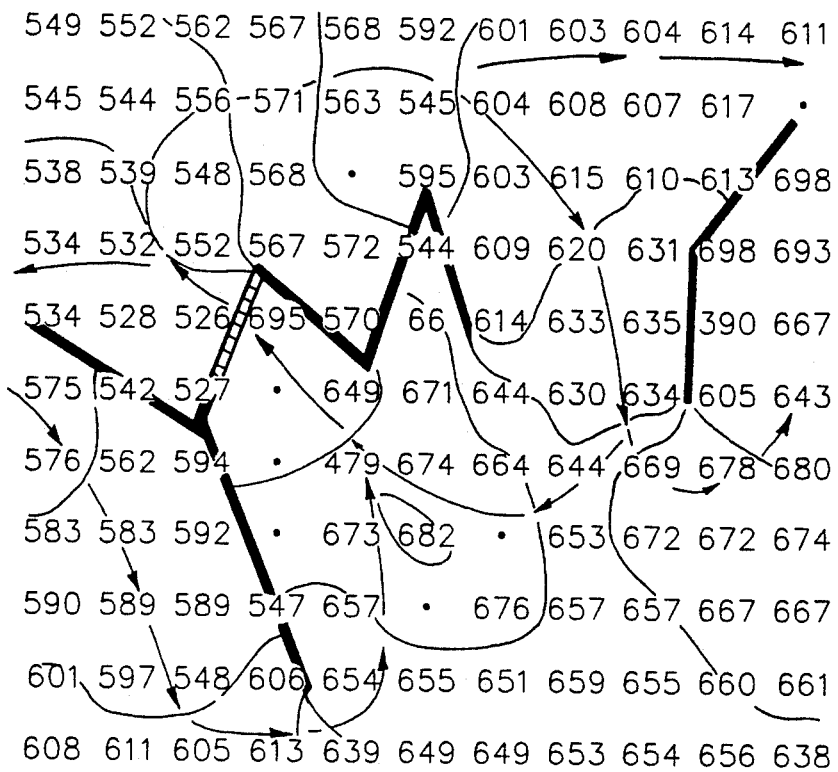
Figure 7F:
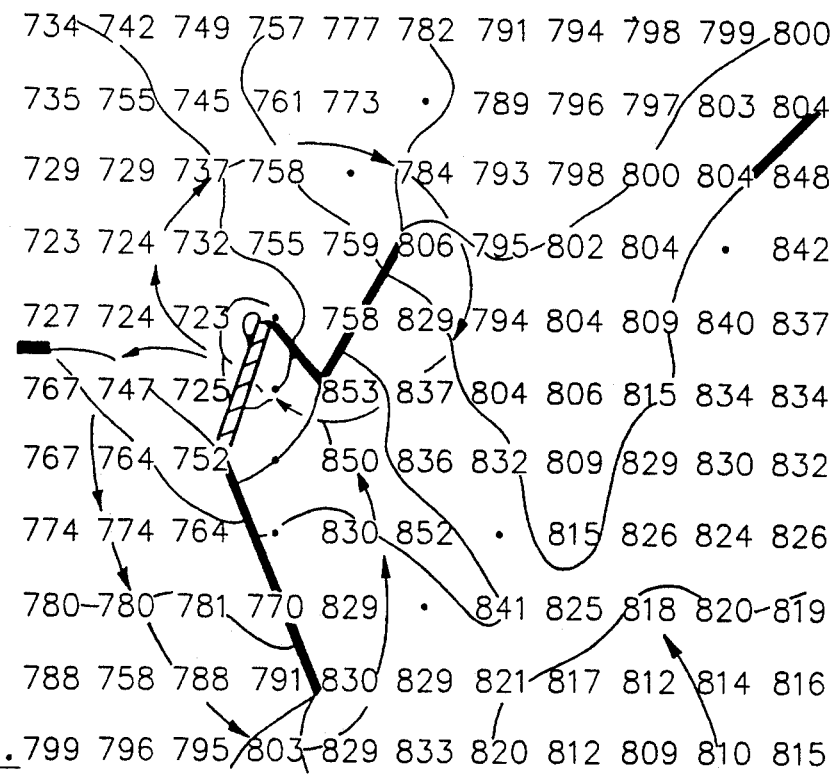
Figure 7G:
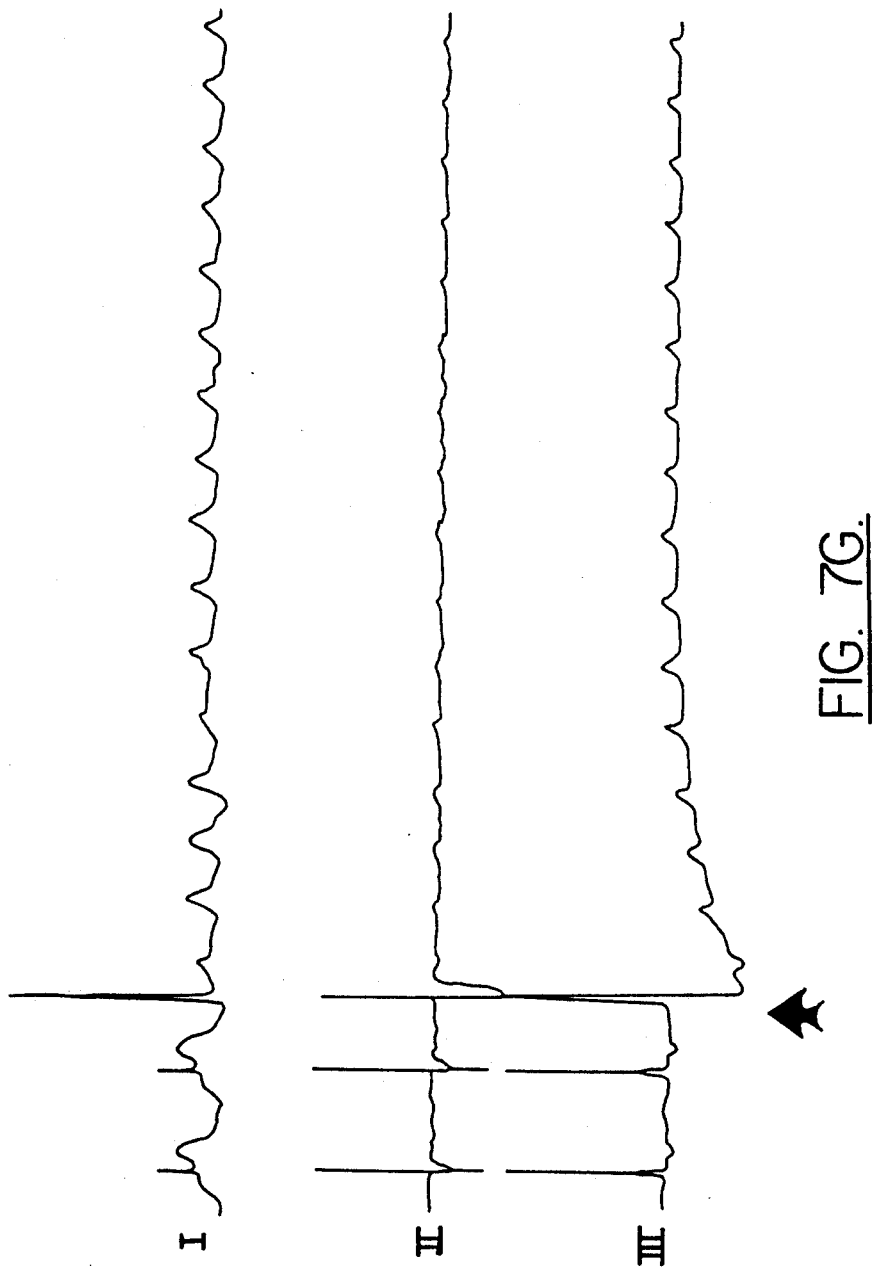
Figure 8A:
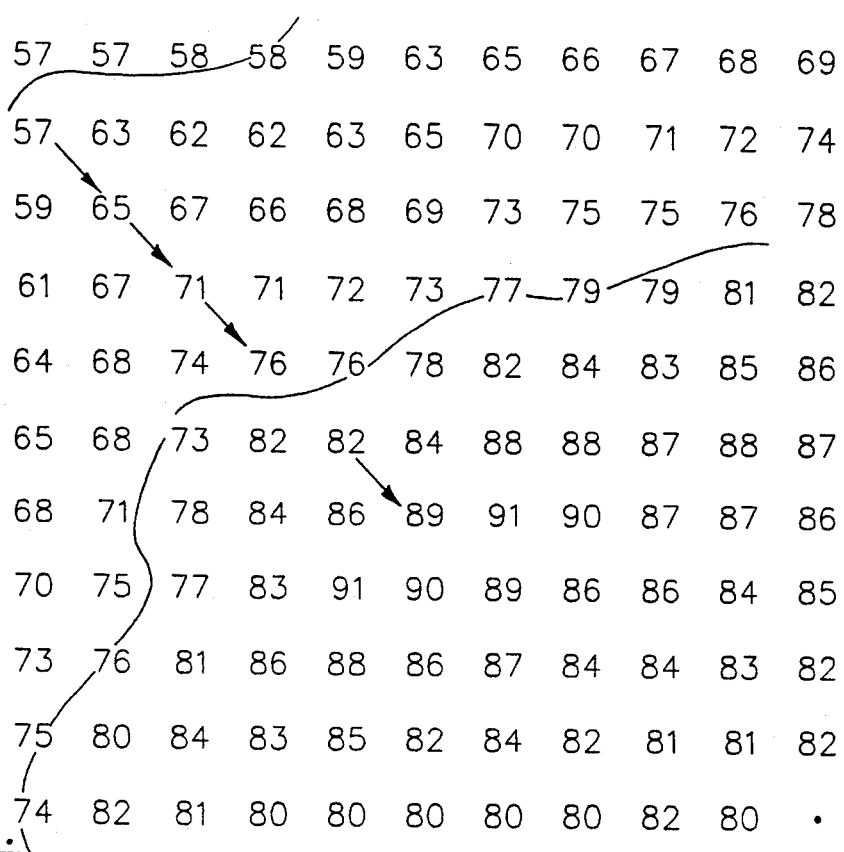
FIGS. 8A-E shows the initiation of sustained monomorphic ventricular tachycardia with a figure of 8 reentry pattern in a second animal in which the S1 was delivered from the right ventricular free wall. The activation times and isochronal maps of the last beat of the 300 ms S1 train (Panel A) as well as those of the first 3 beats of ventricular tachycardia (Panels B-D) induced by a 30 mA S2 stimulus at an S1S2 interval of 230 ms are shown. In panel B, the activation pattern of the first beat post S2 stimulation is compatible with figure of 8 reentry. The initial activation sequence is directed back toward the S1 stimulation site in the direction opposite the S1 activation sequence. Figure of 8 reentry is also seen in the subsequent beats of ventricular tachycardia (Panels C and D). Panel E shows the lead II rhythm strip of ventricular tachycardia induced. Open arrow indicates the first S1 and closed arrow indicates S2. The long axis of the spared myocardial fibers is represented by the double headed arrow at the top of the figure.
Figure 8B:
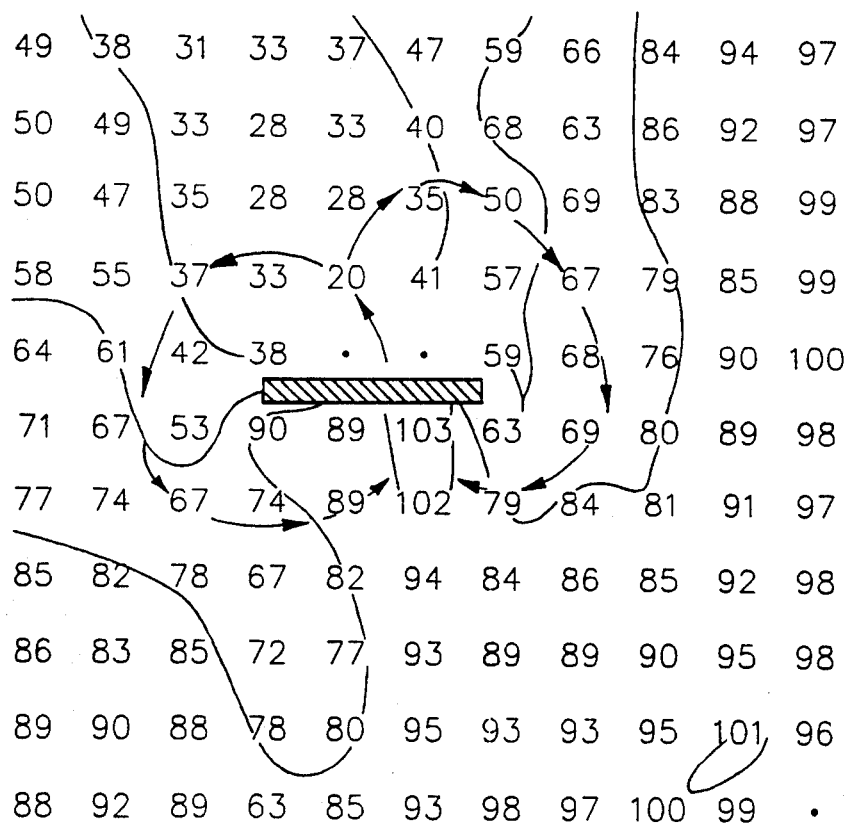
Figure 8C:
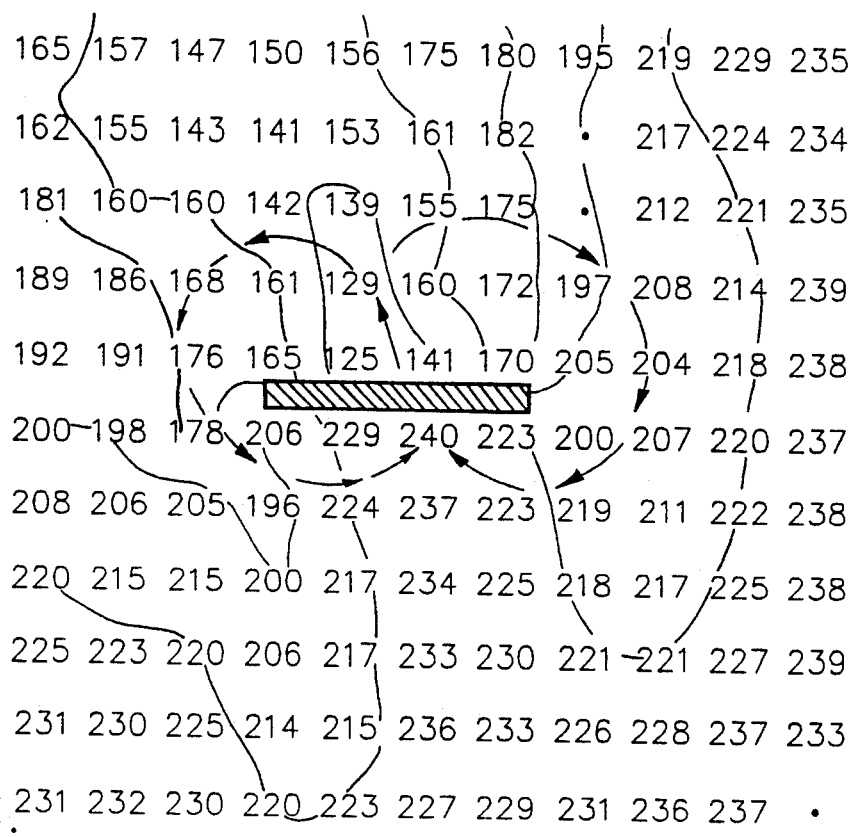
Figure 8D:
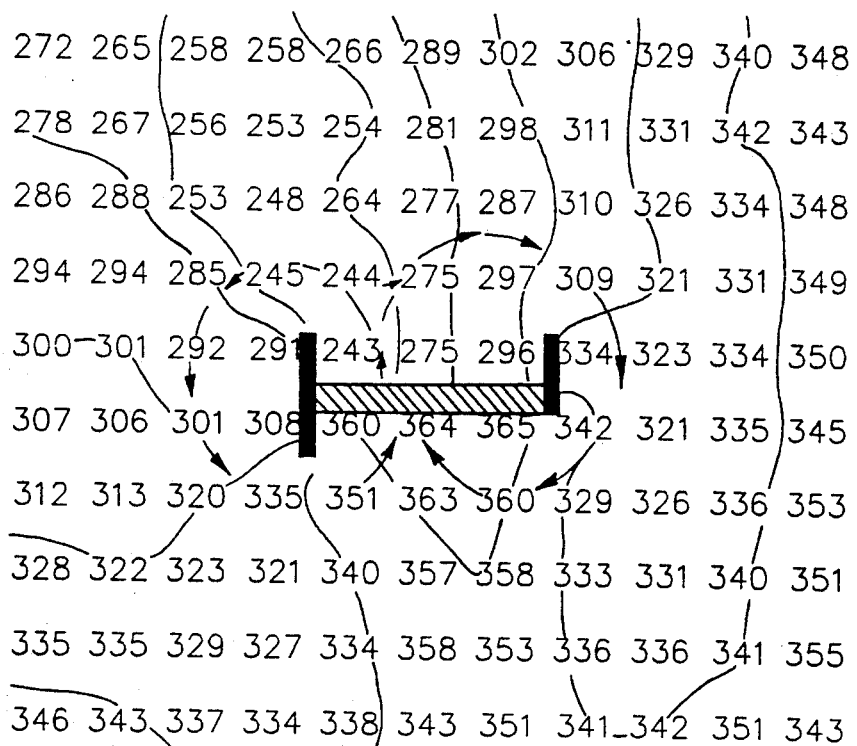
Figure 8E:
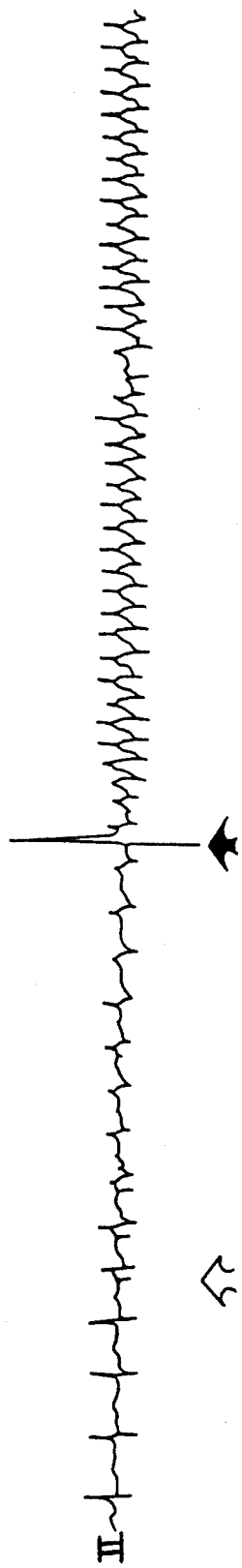
Figure 9A:
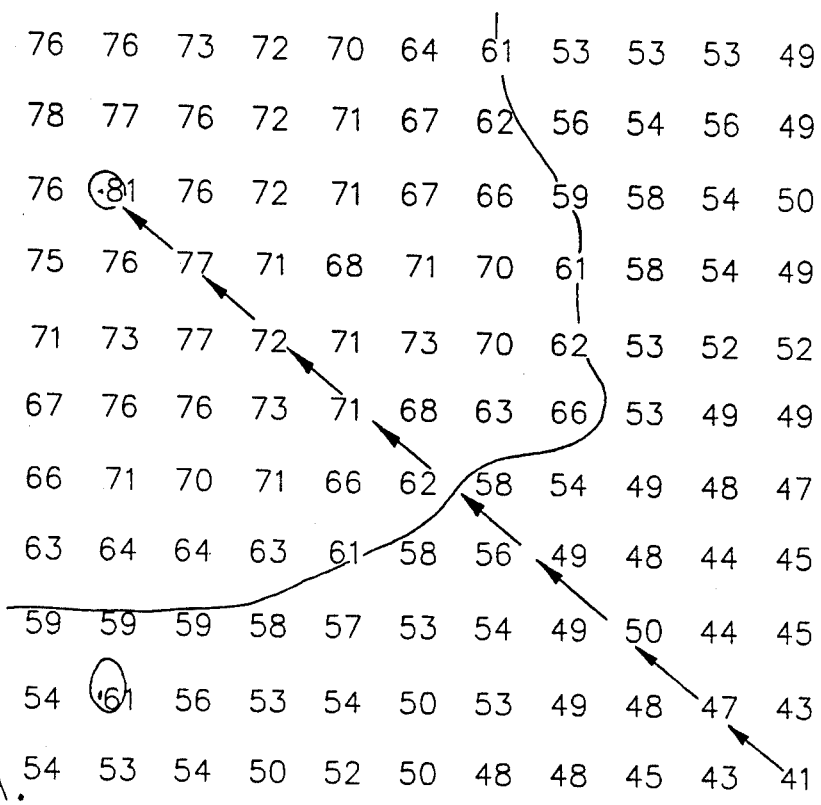
FIGS. 9A-E shows the initiation of sustained monomorphic ventricular tachycardia with a figure of 8 reentry pattern in which the S1 was delivered from the left ventricular free wall in the same animal as for FIG. 8. The activation times and isochronal maps, of the last beat of the 300 ms S1 train (Panel A) as well as those of the first 3 beats of ventricular tachycardia (Panels B-D) induced by a 30 mA S2 stimulus at an S1S2 interval of 230 ms, are shown. In panel B, the activation pattern of the first beat post S2 stimulation is compatible with figure of 8 reentry and once again the initial activation is generally back toward the S1 stimulation site in the direction opposite the S1 activation sequence. Figure of 8 reentry is also seen in subsequent beats (Panels C and D). Panel E shows the lead II rhythm strip of ventricular tachycardia induced. Open arrow indicates the first S1 and closed arrow indicates S2.
Figure 9B:
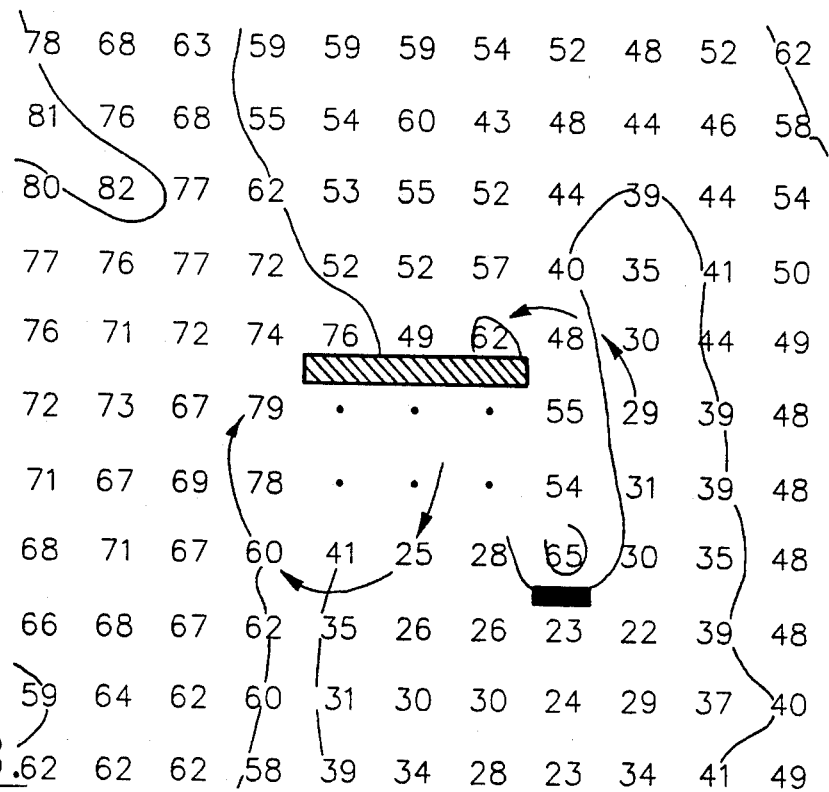
Figure 9C:
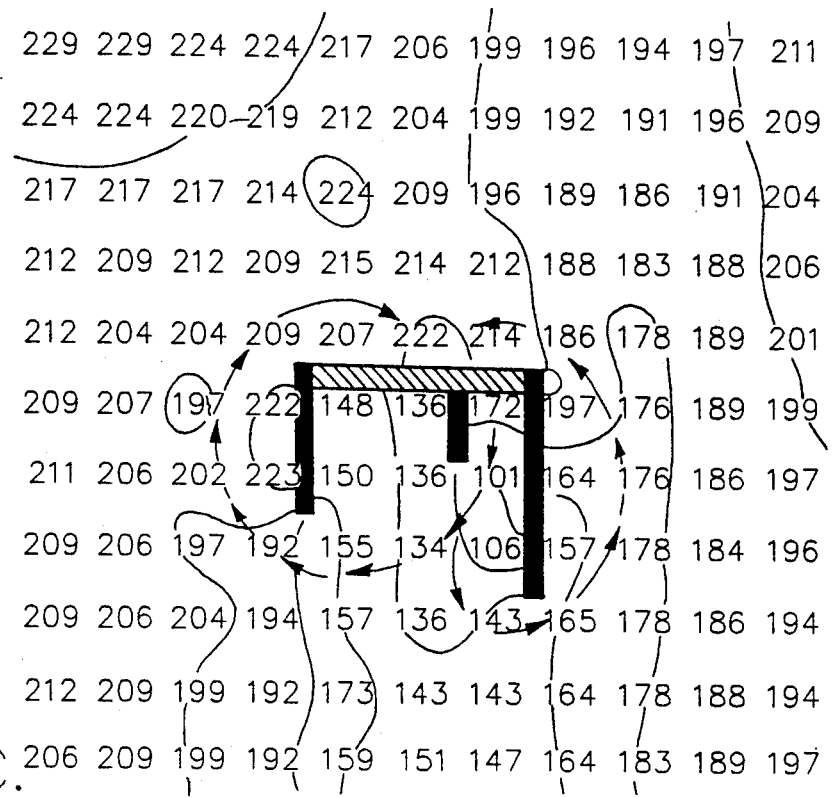
Figure 9D:
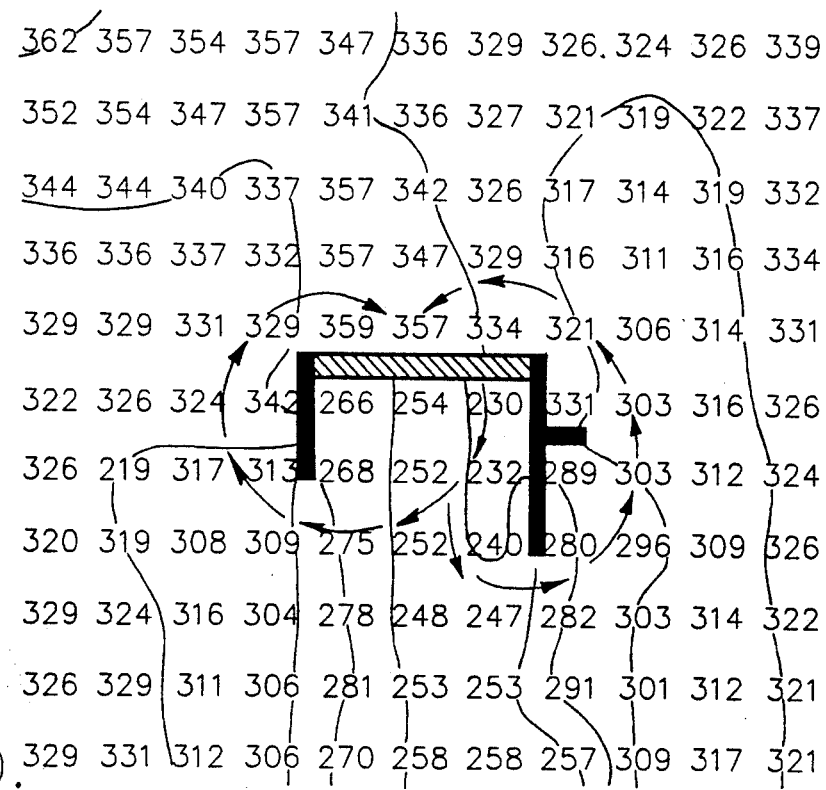
Figure 9E:
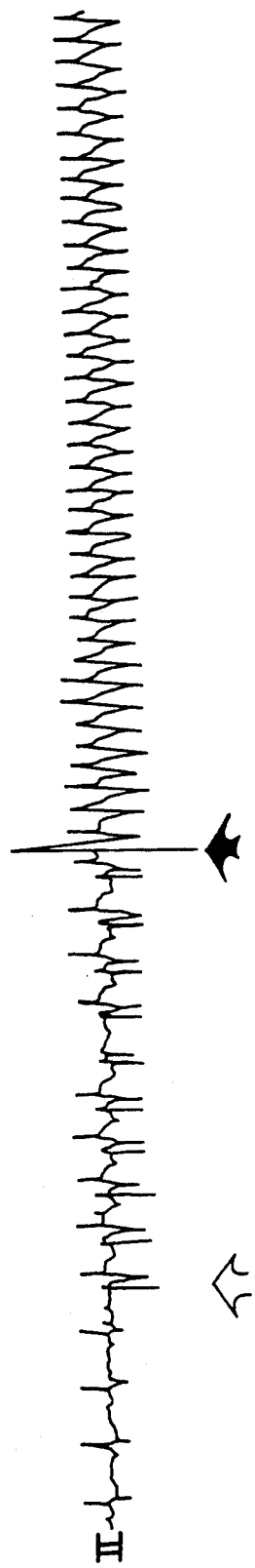

In 19 of the 33 episodes of ventricular tachyarrhythmias induced by stimulation from the various S1 pacing sites, it was possible to identify the initial activation sites of the first beat of the arrhythmia. Earliest post S2 activation was never recorded from the region immediately adjacent to the S2 electrode. In 14 of these 19 episodes initial activation occurred somewhere between the S1 and the S2 stimulation site and generally conducted in the direction away from the S2 electrode and towards the S1 electrode, in the opposite direction to the S1 activation sequence (FIG. 8, 9). In the other 5 episodes the initial post S2 activation of the arrhythmia seemed to conduct into the recording area from outside the plaque (FIG. 7B). In the remaining arrhythmia episodes, the initial activation sites of the first arrhythmia beat could not be identified because of post S2 stimulation saturation of a large percentage of the recording electrodes. However, by the second beat it could be identified that the activation front was in the opposite direction of the S1 activation sequence in 25 of the 33 arrhythmia episodes.

Comparison of Ventricular Tachycardia and Fibrillation Induction. Sustained monomorphic ventricular tachycardia was the only arrhythmia induced in five dogs. In these animals, the mean transmural infarct extent was 80% (Table 1). Ventricular fibrillation was the only arrhythmia induced in two dogs. In these animals, the mean transmural extent of the infarct was 15%. Both ventricular tachycardia and fibrillation were induced in three dogs where the transmural extent of the infarct was 63%.

Conclusions. These data show that the more transmural the infarct and the thinner the layer of spared epicardial tissue, the more likely the figure of 8 reentry pattern will have a longer cycle length and result in ventricular tachycardia rather than ventricular fibrillation.

The foregoing examples are illustrative of the present invention, and are not to be construed as limiting thereof. The invention is defined by the following claims, with equivalents of the claims to be included therein.

That which is claimed is:

1. A closed-heart method for treating ventricular tachycardia in a myocardial infarct patient afflicted with ventricular tachycardia, said method comprising:
   (a) defining the boundaries of a thin layer of spared myocardial tissue positioned between the myocardial infarct scar tissue and the inner surface of the myocardium (the endocardium) of said patient; and then
   (b) ablating said thin layer of spared myocardial tissue by a closed-heart procedure with an ablation catheter.

2. A method according to claim 1, wherein said defining step comprises the step of defining a thin layer having a thickness of up to about 5 millimeters.

3. A method according to claim 1, wherein said defining step comprises the step of defining a thin layer having a thickness of from about 25 to 2 millimeters.

4. A method according to claim 1, wherein said defining step comprises the step of defining a thin layer having an endocardial surface area of at least 15 square centimeters.

5. A method according to claim 1, wherein said defining step comprises the step of defining a thin layer having an endocardial surface area of from about 20 to 40 square centimeters.

6. A method according to claim 1, wherein said defining step is carried out in the absence of ventricular tachycardia.

7. A method according to claim 1, wherein said defining step is carried out by detecting said thin layer of spared myocardial tissue by echocardiography.

8. A method according to claim 1, wherein said defining step is carried out by detecting said infarct overlying said thin layer of spared myocardial tissue by echocardiography.

9. A method according to claim 1, wherein said defining step is carried out by visualization of endocardial fibrosis beneath said thin layer of spared myocardial tissue.

10. A method according to claim 1, wherein said defining step is carried out by electrically stimulating the endocardium to detect an increased pacing threshold.

11. A method according to claim 1, wherein said defining step is carried out with a catheter mounted echocardiographic ultrasound crystal sensor inserted into the interior of the heart of said patient.

12. A method according to claim 1, wherein said defining step is carried out with an echocardiographic ultrasound crystal sensor positioned in the esophagus of said patient.

13. A method according to claim 1, wherein said ablating step comprises destroying all of said thin layer of spared myocardial tissue.

14. A method according to claim 1, wherein said ablating step comprises the step of electrically separating a portion of said thin layer sufficient in size to combat ventricular tachycardia from the remainder of the endocardium.

15. A method according to claim 1, wherein said ablating step comprises the step of creating at least one elongate lesion in said thin layer extending from the endocardium to said myocardial infarct scar tissue, wherein said at least one elongate lesion divides said thin layer into a plurality of electrically separated portions, and wherein each of said portions is incapable of originating ventricular tachycardia.

16. A method according to claim 15, wherein said at least one elongate lesion comprises a plurality of elongate lesions.

17. A method according to claim 1, wherein said ablating step is followed by the step of verifying that said thin layer of spared myocardial tissue is no longer capable of originating a ventricular tachycardia.

18. A method according to claim 17, wherein said verifying step comprises a programmed pacing technique to induce ventricular tachycardia.

19. A closed-heart method for treating ventricular tachycardia in a myocardial infarct patient afflicted with ventricular tachycardia, said method comprising:
 (a) defining the boundaries of a thin layer of spared myocardial tissue positioned between the myocardial infarct scar tissue and the inner surface of the myocardium (the endocardium) of said patient, said thin layer having a thickness up to about five millimeters and an endocardial surface area of at least 15 square centimeters; and then
 (b) ablating said thin layer of spared myocardial tissue by creating at least one elongate lesion in said thin layer extending from the endocardium to said myocardial infarct scar tissue in a closed-heart procedure with an ablation catheter, wherein said at least one elongate lesion is configured to reduce any portion of said thin layer in electrical contact with the remainder of the endocardium to a size, in surface area, sufficient to combat ventricular tachycardia in said patient.

20. A method according to claim 19, wherein said ablating step comprises the step of electrically separating from the remainder of the endocardium a portion of said thin layer sufficient in size, in surface area to combat ventricular tachycardia.

21. A method according to claim 19, wherein said electrically separating step comprises the step of creating a continuous lesion extending from the endocardium to said myocardial infarct scar tissue around said thin layer of spared myocardial tissue, said continuous lesion encircling said thin layer to electrically separate said thin layer from adjacent myocardial tissue.

22. A method according to claim 19, wherein said ablating step comprises the step of creating at least one elongate lesion in said thin layer extending from the endocardium to said myocardial infarct scar tissue, wherein said at least one elongate lesion divides said thin layer into a plurality of electrically separated portions, and wherein each of said portions is reduced to a size, in surface area, sufficient to combat ventricular tachycardia.

23. A method according to claim 19, wherein said at least one elongate lesion comprises a plurality of elongate lesions.

24. A method for prognosing the likelihood of ventricular tachycardia occuring in a myocardial infarct patient not previously diagnosed as afflicted with ventricular tachycardia, said method comprising detecting the boundaries of a thin layer of spared myocardial tissue positioned between the myocardial infarct scar tissue and the inner surface of the myocardium (the endocardium) in said patient.

25. A method according to claim 24, wherein said method is a closed-heart method.

26. A method according to claim 24, wherein said detecting step is carried out by:
 (a) determining if a thin layer of spared tissue exists between the infarct and the endocardium, and then
 (b) creating a map of the locations of the thin layer identified in said determining step to define the thin layer areas, and
 (c) evaluating the dimensions of said thin layer areas to determine if the contiguous portions of said thin layer areas are of sufficient size to support reentrant pathways.

27. A method according to claim 24, wherein said detecting step comprises the step of detecting a thin layer having a thickness of up to about 5 millimeters.

28. A method according to claim 24, wherein said detecting step comprises the step of detecting a thin layer having a thickness of from about 0.25 to 2 millimeters.

29. A method according to claim 24, wherein said detecting step comprises the step of detecting a thin layer having an endocardial surface area of at least 15 square centimeters.

30. A method according to claim 24, wherein said detecting step comprises the step of detecting a thin layer having an endocardial surface area of from about 20 to 40 square centimeters.

31. An apparatus for the ablation treatment of ventricular tachycardia, comprising:
 an intraventricular catheter;
 detecting means for detecting the boundaries of a thin layer of spared endocardial tissue connected to said intraventricular catheter;
 ablation means for ablating said thin layer of spared endocardial tissue connected to said intraventricular catheter; and
 analyzing means operatively associated with said detecting means for prognosing the likelihood of ventricular tachycardia arising from said thin layer.

32. An apparatus according to claim 31, wherein said analyzing means comprises a software program running in a computer.

33. A closed-heart method for treating ventricular tachycardia in a myocardial infarct patient afflicted with ventricular tachycardia, said method comprising:
 (a) defining a thin layer of spared myocardial tissue positioned between the myocardial infarct scar tissue and the inner surface of the myocardium (the endocardium) of said patient; and then
 (b) ablating said thin layer of spaced myocardial tissue by a closed-heart procedure with an ablation catheter;
wherein said ablating step comprises the step of creating a continuous lesion extending from the endocardium to said myocardial infarct scar tissue around said thin layer of spared myocardial tissue, said continuous lesion encircling said thin layer to electrically separate said thin layer from adjacent myocardial tissue.

34. A method according to claim 33, wherein said defining step is carried out in the absence of ventricular tachycardia.

35. A method according to claim 33, wherein said defining step is carried out by detecting said thin layer of spared myocardial tissue by echocardiography.

36. A method according to claim 33, wherein said defining step is carried out by detecting said infarct overlying said thin layer of spared myocardial tissue by echocardiography.

37. A method according to claim 33, wherein said defining step is carried out by visualization of endocardial fibrosis beneath said thin layer of spared myocardial tissue.

38. A method according to claim 33, wherein said defining step is carried out by electrically stimulating the endocardium to detect an increased pacing threshold.

* * * * *

UNITED STATES PATENT AND TRADEMARK OFFICE
CERTIFICATE OF CORRECTION

PATENT NO. : 5,222,501

DATED : 29 June 1993

INVENTOR(S) : Raymond E. Ideker, Gregory P. Walcott

It is certified that error appears in the above-identified patent and that said Letters Patent is hereby corrected as shown below:

Column 4, Line 50, correct "12, 12" to read --12, 12'--.

Column 11, Line 34, correct " With " to read -- with --.

Column 11, Line 45, correct " o " to read -- on --.

Column 14, Claim 3, Line 23, correct " 25 " to read --.25 --.

Signed and Sealed this

Twenty-sixth Day of April, 1994

Attest:

BRUCE LEHMAN

Attesting Officer

Commissioner of Patents and Trademarks